United States Patent [19]

Bugaut et al.

[11] 4,289,495
[45] Sep. 15, 1981

[54] OXIDATIVE DYE COMPOSITIONS CONTAINING A 2,5-DIHYDROXYPHENYLALKANOIC ACID OR SALTS THEREOF AS ANTIOXIDANT

[75] Inventors: Andreé Bugaut, Boulogne-Billancourt; Jean-François Grollier, Paris; Jean-Jacques Vandenboosche, Aulnay-sous-Bois, all of France

[73] Assignee: L'Oreal, Paris, France

[21] Appl. No.: 934,830

[22] Filed: Aug. 18, 1978

[30] Foreign Application Priority Data

Aug. 19, 1977 [LU] Luxembourg ............................ 77994

[51] Int. Cl.³ .............................................. A01K 7/13
[52] U.S. Cl. .......................................... 8/406; 8/408;
562/475; 562/478; 544/160; 568/337;
260/343.3 R; 260/501.1; 260/501.17
[58] Field of Search .................... 562/475, 478; 8/10.2

[56] References Cited

U.S. PATENT DOCUMENTS 4,010,200   3/1977   Kalopissis ............................. 8/10.2
4,123,428  10/1978   Holleger et al. ..................... 562/475

OTHER PUBLICATIONS

Chemical Abst. 85: 130429n, vol. 85, 1976.
Ogura, M. et al., Lloydia, vol. 39, #4, pp. 255–257.

*Primary Examiner*—Paul J. Killos
*Attorney, Agent, or Firm*—Fleit & Jacobson

[57] ABSTRACT

Oxidative dye compositions for keratin fibres are provided which contain a 2,5-dihydroxyphenylalkanoic acid or salt thereof as antioxidant.

28 Claims, No Drawings

OXIDATIVE DYE COMPOSITIONS CONTAINING A 2,5-DIHYDROXYPHENYLALKANOIC ACID OR SALTS THEREOF AS ANTIOXIDANT

DESCRIPTION

The present invention relates to dyeing compositions which are intended for dyeing keratin fibres, and in particular for dyeing human hair, and which comprises a 2,5-dihydroxyphenylalkanoic acid or one of its salts as an antioxidant or reducing agent.

Most of the hair dyeing processes which are currently employed use so-called oxidative dyestuffs, that is to say compounds which are not dyestuffs in themselves but which, by oxidation at the time of use, produce coloured compounds which dye the keratin fibre in situ. This oxidation at the time of use is generally produced using hydrogen peroxide or per-salts, but can also result from simple exposure to atmospheric oxygen.

By virtue of their structure, these oxidative dyestuffs are extremely sensitive to oxidising agents. During use and storage of dyes based on oxidative dyestuffs, in the absence of reducing agents, it has been observed that the dyeing power of the dyes decreases and deteriorates, which can lead to a change in the expected shade; it is also possible to observe a darkening of the dyeing solutions which lose their initial aesthetic and clear appearance. This change in the dyeing power and this darkening of the dyeing solutions are most frequently due to oxidation on contact with air, which can take place both during dissolution of the dyestuffs, whilst stirring, and during storage of the colouring composition in containers which are hermetically sealed but which contain a certain volume of air. The degradation of the dyeing composition can be very considerable if the bottle is closed again after using only part of colouring composition and if the remaining part is not used until several days after removal of the first part.

In the absence of reducing components, very rapid oxidation of the dyestuff solution is also observed immediately after it has been mixed with the oxidising agent; in addition to the unaesthetic appearance due to the rapid blackening, this results in a poorer penetration of the highly oxidisable compounds into the keratin fibre, thus causing a considerable decrease in the development of the colour in situ on the hair.

In order to overcome these disadvantages inherent in dyes based on oxidative dyestuffs, it has already been proposed to introduce, into the dyeing solution, reducing agents such as inorganic sulphites which have been used for a very long time, ascorbic acid (see French Pat. Nos. 1,338,063 and 1,408,167), mercaptans (see German Pat. No. 839,991) and also sodium dithionite (see French Pat. No. 1,052,622).

Unfortunately, all these proposed expedients exhibit disadvantages: ascorbic acid rapidly loses its activity in the basic dyeing medium with the result that the contents of the bottles oxidise very rapidly after the bottles (which may have been kept for several months) are opened; sodium dithionate gives rise to undesirable secondary reactions.

Furthermore, in numerous cases, the oxidative dyestuffs are used as a mixture with direct dyestuffs. These direct dyestuffs, which are mainly nitroaminobenzene dyestuffs, make it possible to shade the oxidative dyestuffs advantageously and, in particular to obtain shades having aesthetic and natural sheens; these direct dyestuffs are reduced or modified by adding too large an amount of reducing agent.

Consequently, reducing agents such as mercaptans, inorganic sulphites or sodium dithionite can only be used in small amounts which are insufficient to ensure satisfactory protection of the oxidative dyestuffs.

Thus, when added in too large a proportion to dyeing compositions based on oxidative dyestuffs, which additionally contain nitro dyestuffs, sodium sulphite modifies the nitro dyestuff and introduces undesirable secondary shades. The amount of sodium dithionite or thio compounds which is necessary for a good protection of the oxidative dyestuffs frequently reduces the nitro compounds in a irreversible manner. Furthermore, larger amounts of these reducing compounds impart, to the dyeing solution, an unpleasant odour which is difficult to mask.

We have discovered that the disadvantages of the above-mentioned reducing agents can advantageously be overcome by completely or partially replacing them by a 2,5-dihydroxyphenylalkanoic acid or one of its salts, of the general formula:

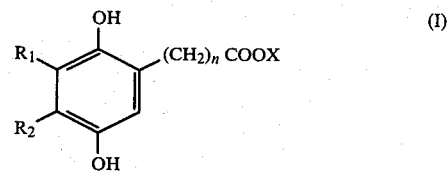

in which $R_1$ and $R_2$ are identical or different and denote hydrogen or a straight- or branched-chain lower alkyl (i.e. $C_1$–$C_4$) group, preferably a methyl, ethyl or propyl group, X denotes hydrogen, an alkali metal such as sodium or potassium, ammonium, or a quaternary alkanolamine radical such as a monoethanolamine, diethanolamine or triethanolamine radical, and n is equal to at least 1 and can have a value from 1 to 4.

The present invention therefore provides dyeing compositions for keratin fibres, and in particular for human hair, which comprises at least one oxidative dyestuff and additionally comprise a 2,5-dihydroxyphenylalkanoic acid or one of its salts, of the formula (I). Typical such acids include homogentisic acid, 2-(2′,5′-dihydroxy-4′-methylphenyl)-acetic acid, 2-(2′,5′-dihydroxy-3′,4′-dimethylphenyl)-acetic acid, (2′,5′-dihydroxyphenyl)propionic acid, and 3-(2′,5′-dihydroxy-4′-methylphenyl)propionic acid.

Some of the compounds of the formula (I) above are believed to be novel. The present invention therefore also provides the compounds of the general formula:

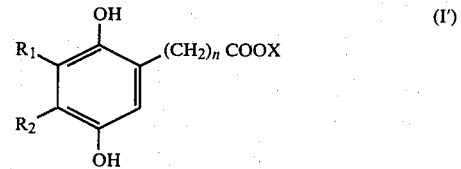

in which $R_1$ and $R_2$ are identical or different and denote hydrogen or a straight- or branched-chain $C_1$–$C_4$ lower alkyl group, preferably a methyl, ethyl or propyl group, at least one of $R_1$ and $R_2$ denoting a lower alkyl group as above defined, X denotes hydrogen, an alkali metal such as sodium or potassium, ammonium, or an alkanolamine radical such as monoethanolamine, diethanolamine or triethanolamine, and n is equal to at least 1 and can have a value ranging from 1 to 4.

The present invention further provides a process for dyeing hair, which employs the abovementioned dyeing composition. Typically the composition is mixed with a cosmetic oxidising agent and the mixture, after homogenisation is applied to the hair for, say, 5 to 45 minutes; the hair is then rinsed and dried.

The compounds of formula (I) have oxidation/reduction potentials which are such that they can act as antioxidants or reducing agents, thus protecting the oxidative dyestuffs present in the dyeing compositions of the invention.

The amount of the compound of the formula (I) used in the dyeing compositions according to the invention is generally 0.05 to 5% by weight, and preferably 0.1 to 3% by weight, relative to the total weight of the dyeing composition.

The compounds (I) according to the invention can be used in association with other known antioxidants such as sulphites, for example sodium bisulphite, mercaptans such as thioglycolic acid or thiolactic acid and their salts, and pyrazolones such as 5-pyrazolones and, in particular, 1-phenyl-3-methylpyrazole-5-one (described in French Pat. No. 1,422,838) which makes it possible to prevent the rapid blackening of the dyestuff solution after mixing them with the oxidising solution.

As mentioned above, it is well known to introduce direct dyestuffs into oxidative dyeing compositions, in particular for the purpose of imparting aesthetic sheens to the shades obtained. These direct dyestuffs are mainly nitro benzene derivatives but can also be, for example, azo or anthraquinone dyestuffs. In the case where dyestuffs of this kind are introduced into the compositions of the present invention, the compounds (I) exhibit the advantage that they do not cause them to deteriorate during storage.

Of course, care should be taken not to associate the compounds (I) with other antioxidants used in amounts such that they are capable of destroying these direct dyestuffs. When conventional reducing agents such as sulphites and mercaptans are used with the reducing agents of the formula (I) in the dyeing compositions of the invention, their concentration should not exceed 1% by weight, relative to the total weight of the dyeing composition.

The oxidative dyestuffs (or oxidative dyestuff precursors) contained in the dyeing compositions of the invention can be, for example, phenylenediamines, aminophenols, aminophenol ethers, aminodiphenylamines or their addition salts with acids.

The oxidative dyestuffs used according to the invention comprise at least one "oxidative base". Para-phenylenediamines, para-aminophenols, ortho-phenylenediamines, ortho-aminophenols and substituted or unsubstituted heterocyclic bases can be used as "oxidative bases" in the compositions according to the invention.

As para-phenylenediamines which can be used in the compositions according to the invention, there may be mentioned primary, secondary and tertiary para-phenylenediamines which are optionally substituted on the benzene ring, and preferably those represented by the general formula:

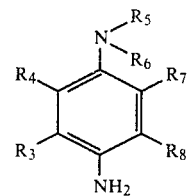

in which: $R_5$ and $R_6$, which are identical or different, represent a hydrogen atom, a straight- or branched-chain lower alkyl group, a mono- or poly-hydroxylic alkyl group or a piperidinoalkyl, carbamylalkyl, dialkylcarbamylalkyl, aminoalkyl, monoalkylaminoalkyl, dialkylaminoalkyl, ω-aminosulphonylalkyl, carboxyalkyl, alkylsulphonoamidoalkyl, arylsulphonoamidoalkyl, morpholinoalkyl, acylaminoalkyl, sulphoalkyl or alkoxyalkyl group, in which groups the alkyl radical preferably contains 1 to 4 carbon atoms, or $R_5$ and $R_6$ together can also form a heterocyclic group having five or six ring members, such as morpholine or piperidine, and $R_3$, $R_4$, $R_7$ and $R_8$ each represent, independently of one another, a hydrogen or halogen atom, a lower alkyl group preferably containing 1 to 4 carbon atoms, or a group -OZ, Z being a hydroxyalkyl, alkoxyalkyl, acylaminoalkyl, carbalkoxyaminoalkyl, mesylaminoalkyl, ureidoalkyl, aminoalkyl or mono- or dialkylaminoalkyl group.

In the above definition, halogen can mean fluorine, bromine or, preferably, chlorine.

As compounds which are particularly effective in the compositions according to the invention, there may be mentioned: para-phenylenediamine, para-toluylenediamine, methoxy-para-phenylenediamine, chloro-para-phenylenediamine, 2,6-dimethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N-mono- and N,N-di-(β-hydroxyethyl)-para-phenylenediamine, 3-methyl-4-amino-N,N-di-(β-hydroxyethyl)-aniline, 3-chloro-4-amino-N,N-di-(β-hydroxyethyl)-aniline, 4-amino-N-ethyl-N-(carbamylmethyl)-aniline, 3-methyl-4-amino-N-ethyl-N-(carbamylmethyl)-aniline, 4-amino-N-ethyl-N-(morpholinoethyl)-aniline, 3-methyl-4-amino-N-ethyl-N-(morpholinoethyl)-aniline, 4-amino-N-(acetylaminoethyl)-aniline, 4-amino-N-ethyl-N-(acetylaminoethyl)-aniline, 3-methyl-4-amino-N-ethyl-N-(acetylaminoethyl)-aniline, 4-amino-N-ethyl-N-(mesylaminoethyl)-aniline, 3-methyl-4-amino-N-ethyl-N-(mesylaminoethyl)-aniline, 4-amino-N-ethyl-N-(β-sulphoethyl)-aniline, 3-methyl-4-amino-N-ethyl-N-(β-sulphoethyl)-aniline, N-(4'-aminophenyl)-morpholine, N-(4'-aminophenyl)-piperidine, 4-amino-N-ethyl-N-(piperidinoethyl)-aniline, 3-methyl-4-amino-N-methylaniline, 2-chloro-4-amino-N-ethyl-N-(sulphonamidomethyl)-aniline, 2-chloro-4-amino-N-ethylaniline, 2-methyl-4-amino-N-(β-hydroxyethyl)-aniline, 2,5-diaminophenoxyethanol and 4-(β-methoxyethyl)-aminoaniline.

These para-phenylenediamines can be introduced into the dyeing composition in the form of the free base or in the form of a salt, for example in the form of the mono-, di- or tri-hydrochloride or -hydrobromide, the sulphate or the tartrate.

Amongst the other "oxidative bases", there may be mentioned: para-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2,5-diaminopyridine, 2-dimethylamino-5-aminopyridine, 2-diethylamino-5-aminopyridine, 2-methyl-6-aminobenzomorpholine, 5-aminoindole, N-methyl-para-aminophenol, orthoaminophenol, para-aminodiphenylamine, ortho-phenylenediamines and their substituted derivatives, and also the "oxidative bases" described in French Pat. No. 2,016,123 of the Applicant Company, of the general formula:

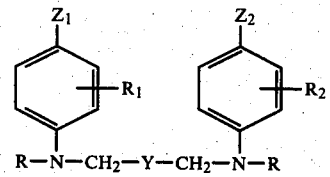

in which: $Z_1$ and $Z_2$, which are identical or different, represent hydroxyl groups or $NHR_3$ groups in which $R_3$ denotes a hydrogen atom or a lower alkyl radical; $R_1$ and $R_2$ which are identical or different, represent either hydrogen atoms or halogen atoms or alkyl groups; R represents a hydrogen atom, an alkyl or hydroxyalkyl group or an aminoalkyl group in which the amino radical can be substituted; and Y represents a radical taken of the formula

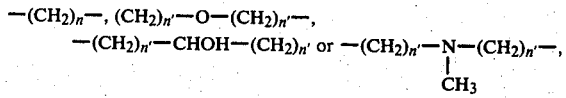

n being 0 or an integer from 1 to 8 and n' being 0 or an integer from 1 to 4, which bases can also be used in the form of their addition salts with acids. Amongst the "oxidative bases" having the formula indicated above, N,N'-(4-aminophenyl)-N,N'-(β-hydroxyethyl)-tetramethylenediamine can be mentioned in particular.

The "oxidative bases" are generally used in the dyeing compositions according to the invention in amounts from 0.005% to 10% by weight and preferably from 0.01% to 5% by weight.

In addition to one or more "oxidative bases", the dyeing compositions of the present invention can also comprise one or more toners which are commonly referred to as couplers. Phenols, meta-diphenols, meta-aminophenols and meta-diamines and their salts may be mentioned as couplers which can be used in the compositions of the invention. These couplers generally correspond to the general formula:

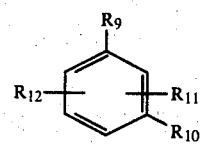

in which: $R_9$ and $R_{10}$, which are identical or different, represent a hydroxyl group or a group —NHR (in which R can be a hydrogen atom or an acyl, ureido, carbalkoxy, carbamylalkyl, alkyl, dialkylcarbamylalkyl, hydroxyalkyl or mesylaminoalkyl group); or a hydrogen atom or an alkoxy or alkyl group, provided that at least one of the substituents $R_9$ and $R_{10}$ represents an OH group; and $R_{11}$ and $R_{12}$ independently represent a hydrogen atom, a branched or linear alkyl group, a halogen atom, an amino, alkylamino, acylamino or ureido group or a group —OZ, Z being a hydroxyalkyl, alkoxyalkyl, mesylaminoalkyl, acylaminoalkyl, ureidoalkyl or carbalkoxyalkyl group.

Amongst the couplers corresponding to the above-mentioned general formula, particular mention can be made of resorcinol, meta-aminophenol, 2,4-diaminoanisole, 2-methyl-5-ureidophenol, 2,6-dimethyl-3-aminophenol, 2-methyl-5-acetylaminophenol, 2,6-dimethyl-5-(acetylamino)-phenol, 3-amino-4-methoxyphenol, 2-methyl-5-[N-(β-hydroxyethyl)-amino]-phenol, meta-phenylenediamine, metatoluylenediamine, N-methyl-meta-aminophenol, 6-methyl-3-aminophenol, 2,4-diaminophenoxyethanol and the salts of these compounds.

Examples of other couplers which can be used in the compositions according to the invention are α-naphthol, heterocyclic compounds such as 6-hydroxybenzomorpholine and 6-aminobenzomorpholine, pyridine derivatives such as 2,6-diaminopyridine, pyrazolones and diketones and their salts.

The diketone compounds which can be used more particularly as couplers in the compositions according to the invention correspond to the formula:

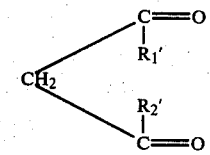

in which $R'_1$ and $R'_2$ each represent, independently of one another, an alkyl group (preferably an alkyl group having 1 to 4 carbon atoms), an alkoxy group, a phenyl group,

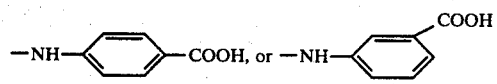

Amongst the pyrazolones which can be used as couplers in the compositions according to the invention, those which are preferably used correspond to the formula:

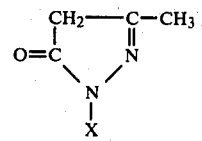

in which X represents a phenyl group which is either unsubstituted or substituted by an —SO₃H group and/or by a halogen (fluorine, bromine or, preferably, chlorine) atom.

The couplers are suitably incorporated into the dyeing compositions of the invention in amounts from 0.005 to 5% by weight and preferably from 0.01 to 3% by weight.

The oxidative dyestuff precursors can also be leuco derivatives such as certain leuco derivatives of indoanilines, for example: 3,5-dimethyl-4-hydroxy-4'-(N,N-dimethylamino)-diphenylamine, 2-acetylamino-2',3,5- trimethyl-4-hydroxy-4'-[N-ethyl-N-(β-mesylaminoethyl)-amino]-diphenylamine, 2-acetylamino-2',5-dimethyl-4-hydroxy-4'-[N-ethyl-N-(carbamylmethyl)-amino]-diphenylamine, 2',3,5,5'-tetramethyl-4-hydroxy-4'-amino-diphenylamine, 2,4-diamino-3-methoxy-4'-hydroxydiphenylamine dihydrochloride 3,5-dimethyl-4-hydroxy-4'-aminodiphenylamine and 2-ureido-4-hydroxy-4'-aminodiphenylamine.

These compounds are suitably incorporated into the dyeing compositions of the invention in amount from 0.005 to 4% by weight.

As direct dyestuffs which can be used in the dyeing compositions of the invention, in association with the oxidative dyestuffs, there may be mentioned nitro dyestuffs, including nitrophenylenediamines, nitroaminophenols, dinitroaminophenols, dinitroaminobenzenes, nitroaminobenzenes and nitrodiphenylamines. These nitro dyestuffs can be, for example: 1-hydroxy-2-amino-4,6-dinitrobenzene, 2-nitro-p-phenylenediamine, 1-amino-2-nitro-4-(N-methylamino)-benzene, 1-hydroxy-2-amino-5-nitrobenzene, 4-nitro-m-phenylenediamine, 1-methoxy-3-nitro-4-[N-(β-hydroxyethyl)-amino]-benzene, 1-(β-hydroxyethyloxy)-3-nitro-4-aminobenzene, 1-methoxy-2-(β-hydroxyethylamino)-5-nitrobenzene, 1-amino-2-nitro-4-[N-(β-hydroxyethyl)-amino]-benzene, 1-(N-methylamino)-2-nitro-4-[N,N-bis-(β-hydroxyethyl)-amino]-benzene, 1-(N-methylamino)-2-nitro-4-[N-methyl-N-(β-hydroxyethyl)-amino]-benzene, 1-hydroxy-3-nitro-4-[N-(β-hydroxyethyl)-amino]-benzene, 1-hydroxy-2,6-dimethyl-3-nitro-4-[N-(β-hydroxyethyl)-amino]-benzene, 4-nitro-o-phenylenediamine, 1-hydroxy-2-amino-4-nitrobenzene, 1-hydroxy-2-nitro-4-aminobenzene, 1,4-bis-[N-(β-hydroxyethyl)-amino]-2-nitrobenzene, 1-amino-2-[N-(β-hydroxyethyl)-amino]-5-nitrobenzene, 1,4,4-tris-N-(β-hydroxyethyl)-2-nitro-p-phenylenediamine, 2-[N,N-bis-(β-hydroxyethyl)-amino]-5-nitrophenol, 1-amino-2-[tris-(hydroxymethyl)-methyl]-amino-5-nitrobenzene, 1-[N-(β-hydroxyethyl)-amino]-2-nitrobenzene, 1,4,4-tris-N-(β-hydroxyethyl)-3-nitro-p-phenylenediamine, 2-nitro-4'-[bis-(β-hydroxyethyl)-amino]-diphenylamine, 2-nitro-4'-hydroxydiphenylamine, 2-nitro-4-aminodiphenylamine, 1-amino-3-nitro-4-[N-(β-hydroxyethyl)-amino]-benzene, 1-hydroxy-2-[N-bis-(β-hydroxyethyl)-amino]-5-nitrobenzene and 1-amino-2-nitro-4-[4-(β-hydroxyethyl)-amino]-5-chlorobenzene.

The direct dyestuffs are suitably incorporated into the dyeing compositions of the invention in amounts from 0.005% to 3% by weight.

The dyeing compositions according to the invention are suitable in the form of gellable compositions or in the form of creams.

Gellable compositions can be obtained from polyoxyethyleneated or polyglycerolated non-ionic compounds in the presence of solvents, or from soaps of liquid fatty acids such as oleic acid or isostearic acid, in the presence of solvents in an aqueous vehicle.

The fatty acids are generally used at concentrations of 0.5 to 15% by weight to form the soaps.

The alkalising agents used to form the soaps include sodium hydroxide, potassium hydroxide, ammonia, monoethanolamine, diethanolamine, triethanolamine and mixtures thereof.

Amongst the polyoxyethyleneated non-ionic compounds, there may be mentioned, in particular, oxyethyleneated nonylphenol containing 4 mols of ethylene oxide and oxyethyleneated nonylphenol containing 9 mols of ethylene oxide.

These constituents are preferably present at concentrations of 5 to 60% by weight.

Amongst the polyglycerolated non-ionic compounds, there may be mentioned, in particular, glycerolated oleyl alcohol containing 2 mols of glycerol and glycerolated oleyl alcohol containing 4 mols of glycerol.

These constituents are preferably present at concentrations of 5 to 60% by weight.

Amongst the solvents which can be used, there may be mentioned ethyl and isopropyl alcohols, and glycols or glycol ether such as the monomethyl, ethyl and butylethers of ethylene glycol, propylene glycol, carbitol and butylcarbitol.

These constituents are preferably present at concentrations of 2 to 20% by weight.

All the concentrations are indicated relative to the total weight of the dyeing composition.

When the dyeing compositions are in the form of creams, their formulation is essentially based on soaps or fatty alcohols in the presence of emulsifiers, in an aqueous vehicle.

The soaps can be formed from natural or synthetic fatty acids having from 12 to 18 carbon atoms, such as lauric acid, myristic acid and palmitic acid, and alkalising agents such as sodium hydroxide, potassium hydroxide, ammonia, monoethanolamine, diethanolamine, triethanolamine or mixtures thereof. The fatty acids are preferably present in the dyeing creams of the invention at concentrations from 10 to 30% by weight.

The creams can also be formulated from natural or synthetic fatty alcohols having 12 to 18 carbon atoms, mixed with emulsifiers. Amongst these fatty alcohols, there may be mentioned, in particular, lauryl alcohol, alcohols derived from copra fatty acids, myristyl alcohol, cetyl alcohol, stearyl alcohol and hydroxystearyl alcohol. The concentrations of fatty alcohols in the creams of the invention is generally 5 to 25% by weight.

The emulsifiers which can be used in the compositions according to the present invention can be polyoxyethyleneated or polyglycerolated fatty alcohols such as, for example, polyoxyethyleneated oleyl alcohol containing from 10 to 30 mols of ethylene oxide, polyoxyethyleneated cetyl alcohol containing from 6 to 10 mols of ethylene oxide, polyoxyethyleneated lauryl alcohol containing 12 mols of ethylene oxide, polyoxyethyleneated cetyl/stearyl alcohol containing 10 or 15 mols of ethylene oxide, polyoxyethyleneated oleyl/cetyl alcohol containing 30 mols of ethylene oxide, polyoxyethyleneated stearyl alcohol containing 10, 15 or 20 mols of ethylene oxide, polyglycerolated oleyl alcohol containing 4 mols of glycerol and synthetic fatty alcohols which contain between 9 and 15 carbon atoms and are polyoxyethyleneated with 5 or 10 mols of ethylene oxide; polyoxyethyleneated castor oil can also be used. These non-ionic emulsifiers are generally present in the dyeing compositions of the invention in an amount from 1 to 25½ by weight.

Other emulsifiers which can be used according to the invention include alkyl-sulphates which may or may not be oxyethyleneated, such as sodium lauryl-sulphate, ammonium lauryl-sulphate, sodium cetyl-/stearyl-sulphate, triethanolamine cetyl-/stearyl-sulphate, monoethanolamine laurylsulphate or triethanolamine laurylsulphate, the sodium salt of the sulphate half-ester of oxyethyleneated lauryl alcohol containing, for example, 2.2 mols of ethylene oxide and the monoethanolamine salt of the sulphate half-ester of oxyethyleneated lauryl alcohol containing, for example, 2.2 mols of ethylene oxide.

These constituents are preferably present in the dyeing compositions of the invention at concentrations of 1 to 15% by weight.

In addition to the soaps, fatty alcohols and emulsifiers, the creams according to the invention can contain adjuvants, such as fatty amides, which are usually employed in compositions of this kind.

Amongst the fatty amides which are preferably used are the mono- or di-ethanolamides of acids derived from copra, of lauric acid or of oleic acid at concentrations up to 10% by weight, relative to the total weight of the composition.

The dyeing compositions according to the invention can also contain, for example, sequestering agents such as ethylenediaminetetraacetic acid or diethylenetriaminepentaacetic acid or their salts, thickeners and perfumes.

The pH of the dyeing compositions of the invention is generally 6 to 11 and preferably 8 to 11. It can be adjusted by adding a suitable alkalising agent such as ammonia, monoethanolamine, diethanolamine, triethanolamine or mixtures thereof.

The dyeing compositions according to the invention which are based on oxidative dyestuffs are used for dyeing hair in accordance with a process which employs development by means of an oxidising agent.

In this dyeing process using development by means of an oxidising agent, an oxidising agent is mixed, as a powder or in solution, with the dyeing composition, the mixture is applied to the hair for a period of time which generally varies from 5 to 45 minutes and the hair is then rinsed and dried. The oxidising agents used can be hydrogen peroxide, urea peroxide, per-salts such as ammonium persulphate, sodium persulphate or potassium persulphate, barium dioxide or silver carbonate. The concentrations of the oxidising solutions in generally 0.1 to 6% by weight.

When applied to natural hair or hair which has already been dyed, the dyeing compositions based on oxidative dyestuffs according to the invention make it possible to obtain a uniform coloration which develops gradually.

The compounds of the formula (I) can be prepared in accordance with two known processes A and B, depending on whether n=1 or 2 or n=3 or 4.

Process A makes it possible to obtain the compounds in which n=1 or 2 and comprises the following steps:

(1) Friedel/Crafts reaction on the compounds (II)

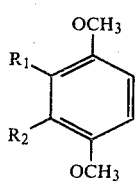

in the presence of e.g. AlCl$_3$, using acetyl or propionyl chloride to obtain the compounds (III):

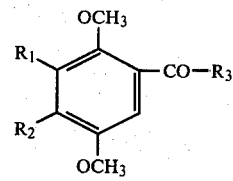

in which R$_3$=CH$_3$ or C$_2$H$_5$.

(2) Willgerodt reaction (for example with sulphur and morpholine) on the compounds (III) to obtain the aceto- or propiono-thiomorpholides (IV)

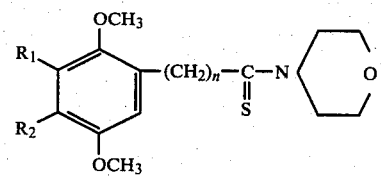

in which n=1 or 2.

(3) Alkaline hydrolysis of the compounds (IV) to obtain the compounds (V):

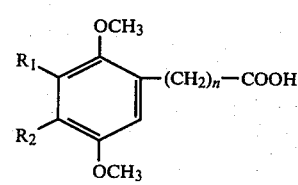

in which n=1 or 2.

(4) Demethoxylation of the compounds (V), using hydrobromic or hydriodic acid to obtain the acids (I):

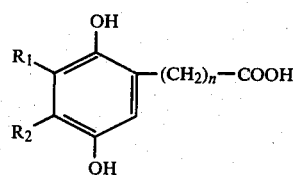

in which n=1 or 2.

Process B for the preparation of compounds (I) in which n=3 or 4 comprises the following steps:

(1) Action of succinic or glutaric anhydride, in the presence of AlCl$_3$, on the compounds (II):

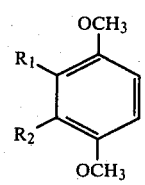

to obtain the compounds (VI):

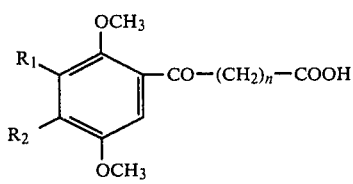 (VI)

in which n=2 or 3.

(2) Reduction of the compounds (VI) by the Clemmensen method (Zn amalgam, HCl) or, preferably, using hydrazine to obtain the compounds (V):

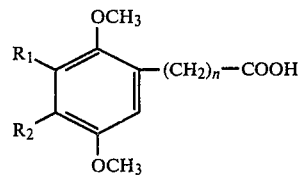 (V)

in which n=3 or 4.

(3) Demethoxylation of the compounds (V), using hydrobromic or hydriodic acid to obtain the acids (I):

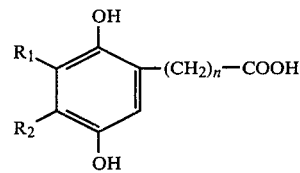 (I)

in which n=3 or 4.

The acids of the formula (I), obtained in accordance with processes A and B above, can then be converted, in known manner, into alkali metal, ammonium or alkanolamine salts.

The following Examples illustrate the preparation of some of the new compounds of the formula (I') namely 2-(2',5'-dihydroxy-4'-methylphenyl)-acetic acid, 2-(2',5'-dihydroxy-3',4'-dimethylphenyl)-acetic acid and 3-(2',5'-dihydroxy-4'-methylphenyl)-propionic acid.

EXAMPLE 1

Preparation of 2-(2',5'-dihydroxy-4'-methylphenyl)-acetic acid

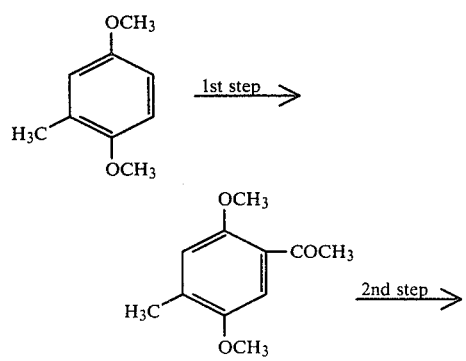

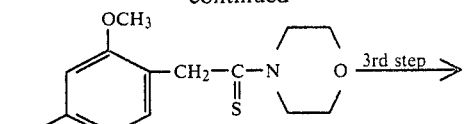

-continued

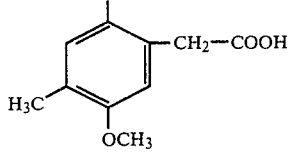

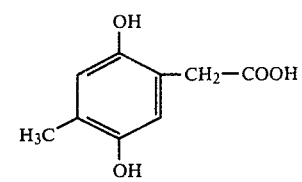

1st step: Preparation of 2,5-dimethoxy-4-methylacetophenone.

1 mol (152 g) of 2,5-dimethoxytoluene is introduced, whilst stirring, into 230 ml of acetyl chloride at −10° C. 160 g of aluminium chloride are then added in the course of 3 hours, whilst stirring and keeping the temperature of the reaction medium at between −10° and 0° C. When the addition has ended, the mixture is stirred for a further 3 hours at between −10° and 0° C. The reaction medium is then poured onto 1 kg of crushed ice to which 110 ml of hydrochloric acid (d=1.19) have been added. After a few hours, the reaction product which has precipitated is filtered off. After washing with water, a 2 N solution of sodium hydroxide and then again with water, the 2,5-dimethoxy-4-methylacetophenone is recrystallised from ethanol. After drying in vacuo, it melts at 75° C.

| Analysis | Calculated for $C_{11}H_{14}O_3$ | Found |
|---|---|---|
| C % | 68.04 | 68.09 |
| H % | 7.21 | 7.00 |

2nd step: Preparation of (2,5-dimethoxy-4-methylphenyl) acetothiomorpholide.

0.7 mol (136 g) of 2,5-dimethoxy-4-methylacetophenone is heated under reflux for 8 hours in the presence of 1.05 mol (33.6 g) of sulphur in 92 g of morpholine. The reaction medium is then poured into 500 g of ice-cooled water. The reaction product precipitates in the form of a gum. After recrystallisation from ethanol and then acetone and after drying in vacuo, the product melts at 121° C.

| Analysis | Calculated for $C_{15}H_{21}SNO_3$ | Found |
|---|---|---|
| C % | 61.02 | 60.82 |
| H % | 7.12 | 7.30 |
| S % | 10.85 | 11.19 |
| N % | 4.75 | 4.99 |

3rd step: Preparation of 2-(2',5'-dimethoxy-4'-methylphenyl) acetic acid.

0.54 mol (160 g) of (2,5-dimethoxy-4-methylphenyl) acetothiomorpholide is heated under reflux for 4 days in 700 ml of an aqueous-ethanolic solution (75% of ethanol, 25% of H₂O) containing 4 mols (160 g) of sodium hydroxide in solution. The alcohol is then driven off in vacuo, 700 ml of water are added and the reaction medium is again heated to the reflux temperature and filtered at the boil in order to remove a small amount of insoluble material. After cooling, the 2-(2',5'-dimethoxy-4'-methylphenyl)-acetic acid is precipitated by adding hydrochloric acid. The white precipitate obtained is filtered off, washed with water and recrystallised from ethanol. After drying in vacuo, it melts at 128° C.

| Analysis | Calculated for $C_{11}H_{14}O_4$ | Found |
|---|---|---|
| C % | 62.86 | 62.93 |
| H % | 6.66 | 6.65 |

4th step: Preparation of 2-(2',5'-dihydroxy-4'-methylphenyl)-acetic acid.

0.285 mol (60 g) of 2-(2',5'-dimethoxy-4'-methylphenyl)-acetic acid is heated under reflux for 5 hours in 480 ml of 48% strength hydrobromic acid.

After cooling, the acid obtained is filtered off and, after recrystallisation from alcohol and drying in vacuo, melts at 178° C.

| Analysis | Calculated for $C_9H_{10}O_4$ | Found |
|---|---|---|
| C % | 59.34 | 59.30 |
| H % | 5.50 | 5.78 |

EXAMPLE 2

Preparation of 2-(2',5'-dihydroxy-3',4'-dimethylphenyl)-acetic acid.

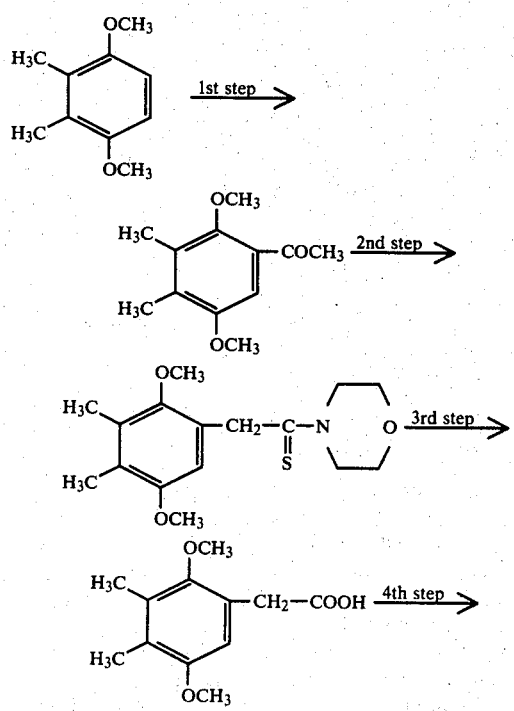

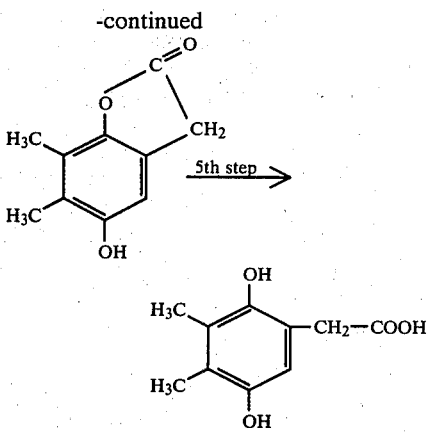

1st step: Preparation of 2,5-dimethoxy-3,4-dimethylacetophenone.

0.15 mol (25 g) of 2,3-dimethyl-1,4-dimethoxybenzene is introduced, whilst stirring, into 35 ml of acetyl chloride at −10° C. 24 g of aluminium chloride are then added gradually, whilst keeping the temperature at between −10° and −5° C. When the addition has ended, the reaction medium is left to stand for 3 hours at about −5° C. and is then poured onto 170 g of crushed ice to which 17 ml of hydrochloric acid (d=1.19) have been added. The thick oil which precipitates is separated off by decantation. This oil distils at between 106° and 107° C. under a pressure of 0.1 mm Hg.

| Analysis | Calculated for $C_{12}H_{16}O_3$ | Found |
|---|---|---|
| C % | 69.23 | 69.30 |
| H % | 7.69 | 7.64 |

2nd step: Preparation of (2,5-dimethoxy-3,4-dimethylphenyl) acetothiomorpholide.

0.33 mol (69.3 g) of 2,5-dimethoxy-3,4-dimethylacetophenone is heated under reflux for 10 hours in the presence of 0.5 mol (16 g) of sulphur in 43.5 g of morpholine. The reaction medium is then poured onto 250 g of crushed ice. The reaction product precipitates in the form of a gum.

The gummy product is treated with 100 ml of ethanol under reflux. The mixture is filtered at the boil. On cooling, the acetothiomorpholide obtained crystallises. After recrystallisation from acetone and drying in vacuo, it melts at 108° C.

| Analysis | Calculated for $C_{16}H_{23}NSO_3$ | Found |
|---|---|---|
| C % | 62.13 | 62.12 |
| H % | 7.44 | 7.30 |
| N % | 4.53 | 4.67 |
| S % | 10.36 | 10.66 |

3rd step: Preparation of 2-(2',5°-dimethoxy-3',4'-dimethylphenyl)-acetic acid.

0.217 mol (67 g) of (2,5-dimethoxy-3,4-dimethylphenyl)-acetothiomorpholide is heated under reflux for 10 hours in 400 ml of an aqueous-ethanolic solution (65% of ethanol, 35% of H₂O) containing 1.7 mol (68 g) of sodium hydroxide. The alcohol is driven off in vacuo, 300 ml of water are added and the reaction medium is again heated to the reflux temperature and filtered at the boil in order to remove a small amount of insoluble material. After cooling, the 2-(2',5'-dimethoxy-3',4'-dimethylphenyl) acetic acid is precipitated by adding hydrochloric acid. The product is filtered off, washed with water, recrystallised from alcohol and dried in vacuo. It melts at 109° C.

| Analysis | Calculated for $C_{12}H_{16}O_4$ | Found |
|---|---|---|
| C % | 64.28 | 64.08 |
| H % | 7.14 | 7.03 |

4th and 5th steps: Preparation of 2-(2',5'-dihydroxy-3',4'-dimethylphenyl)-acetic acid with isolation of the intermediate lactone.

0.3 mol (67.2 g) of 2-(2',5'-dimethoxy-3',4'-dimethylphenyl)-acetic acid is heated under reflux for 1 hour in 400 ml of hydriodic acid to which 130 ml of acetic acid have been added, the fractions having boiling points below 70° C. being removed by distillation as they are formed. The reflux temperature of the reaction medium gradually reaches 115° C.

From 95° C., the reaction product precipitates in the form of a lactone in the reaction medium.

The lactone is filtered off and washed with water. After drying in vacuo, it melts at 220° C.

The lactone obtained is dissolved in 100 ml of a 10 N solution of sodium hydroxide to which 20 g of sodium sulphite have been added. The solution is heated for 20 minutes at 90° C. It is filtered hot. After cooling, the filtrate is acidified to pH 2 using 20% strength sulphuric acid and the reaction product is then extracted with ether. The ether is driven off in vacuo. The crude product thus obtained is recrystallised from a mixture of alcohol, chloroform and petroleum ether. After drying in vacuo, it melts at 176° C.

| Analysis | Calculated for $C_{10}H_{12}O_4$ | Found |
|---|---|---|
| C % | 61.22 | 61.28 |
| H % | 6.12 | 6.29 |

EXAMPLE 3

Preparation of 3-(2',5'-dihydroxy-4'-methylphenyl)-propionic acid

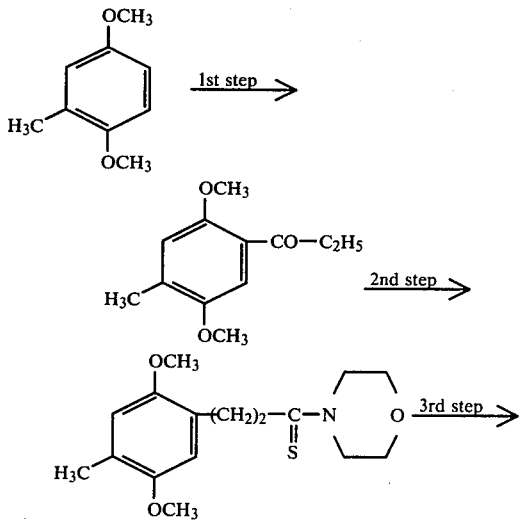

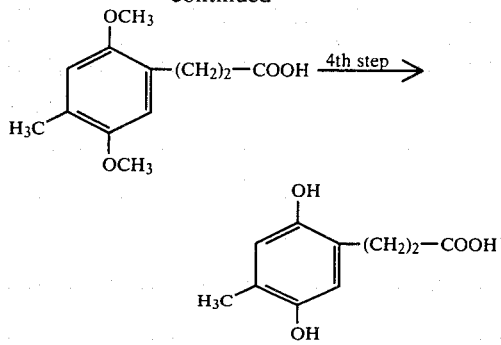

1st step: Preparation of 2,5-dimethoxy-4-methyl-propiophenone.

0.3 mol (50 g) of 2,5-dimethoxytoluene is introduced, whilst stirring, into 70 ml of propionyl chloride at −10° C. 48 g of aluminium chloride are added in the course of 3 hours, whilst stirring and keeping the temperature at about −10° C. When the addition has ended, the mixture is stirred for a further 3 hours at this temperature. The reaction medium is then poured onto 1 kg of crushed ice to which 33 ml of hydrochloric acid (d: 1.19) have been added.

The reaction medium is left to stand for a few hours and the product obtained is then filtered off. After washing with water, a 2 N solution of sodium hydroxide and again with water, the product is recrystallised from alcohol. After drying, it melts at 76° C.

| Analysis | Calculated for $C_{12}H_{16}O_3$ | Found |
|---|---|---|
| C % | 69.23 | 69.03 |
| H % | 7.69 | 7.52 |

2nd step: Preparation of (2,5-dimethoxy-4-methylphenyl) propionothiomorpholide.

1 mol (208 g) of 2,5-dimethoxy-4-methylpropiophenone is heated under reflux for 8 hours in the presence of 1.5 mol (48 g) of sulphur in 131 g of morpholine. The reaction medium is then poured into 800 g of ice-cooled water. The reaction product precipitates and is filtered off and dissolved in 1 liter of acetone under reflux. The solution is filtered. After cooling, the propionothiomorpholide precipitates in the form of crystals. It is filtered off and dried in vacuo. It melts at 156° C.

| Analysis | Calculated for $C_{16}H_{23}NSO_3$ | Found |
|---|---|---|
| C % | 62.13 | 61.94 |
| H % | 7.44 | 7.55 |
| N % | 4.53 | 4.61 |
| S % | 10.36 | 10.50 |

3rd step: Preparation of 3-(2',5'-dimethoxy-4'-methylphenyl) propionic acid.

0.18 mol (58 g) of (2,5-dimethoxy-4-methylphenyl)-propionothiomorpholide is heated under reflux for 8 hours in 350 ml of an aqueous-ethanolic solution (65% of ethanol, 35% of $H_2O$) containing 1.5 mols (60 g) of sodium hydroxide. The alcohol is driven off in vacuo and 250 ml of water are added. The reaction medium is again heated to the reflux temperature and filtered at the boil. After cooling the filtrate, the 3-(2',5'-dimethoxy-4'-methylphenyl)-propionic acid precipitates. It is filtered off, washed with water and recrystallised from alcohol. After drying in vacuo, it melts at 111° C.

| Analysis | Calculated for $C_{12}H_{16}O_4$ | Found |
|---|---|---|
| C % | 64.29 | 64.30 |
| H % | 7.14 | 7.14 |

4th step: Preparation of 3-(2',5'-dihydroxy-4'-methylphenyl) propionic acid.

0.18 mol (40 g) of 3-(2',5'-dimethoxy-4'-methylphenyl)-propionic acid is heated under reflux in 300 ml of 48% strength hydrobromic acid. After cooling, the acid obtained precipitates. It is filtered off, dried and recrystallised from a mixture of ethanol, chloroform and petroleum ether. After drying, it melts at 181° C.

| Analysis | Calculated for $C_{10}H_{12}O_4$ | Found |
|---|---|---|
| C % | 61.22 | 61.17 |
| H % | 6.12 | 6.26 |

The following Examples further illustrate dyeing compositions according to the present invention:

EXAMPLE 4

The following dyeing compositions are prepared:

| CONSTITUENTS | A | B | C |
|---|---|---|---|
| Para-toluylenediamine base | 1.7 g | — | — |
| 4-[N-(β-Methoxyethyl)-amino]-aniline dihydrochloride | — | 1.6 g | 0.18 g |
| Para-aminophenol base | 0.3 g | 0.3 g | 0.4 g |
| Resorcinol | 0.5 g | 0.2 g | 0.03 g |
| Meta-aminophenol | 0.2 g | 0.25 g | 0.04 g |
| 2-Methyl-5-[N-(β-hydroxyethyl)-amino]-phenol | — | 0.02 g | — |
| 2,4-Diaminoanisole sulphate | 0.13 g | — | — |
| 2,4-Diaminophenoxyethanol dihydrochloride | — | 0.02 g | 0.02 g |
| 1-Methoxy-3-nitro-4-[N-(β-hydroxyethyl)-amino]-benzene | — | — | 0.52 g |
| 1-(β-Hydroxyethyloxy)-3-nitro-4-aminobenzene | — | — | 0.1 g |
| Oxyethyleneated nonylphenol containing 4 mols of E.O., sold under the name "Remcopal 334" by Messrs. Gerland | 22 g | 22 g | 22 g |
| Oxyethyleneated nonylphenol containing 9 mols of E.O., sold under the name of "Remcopal 349" by Messrs. Gerland | 22 g | 22 g | 22 g |
| Butylcellosolve | 8 g | 8 g | 8 g |
| Propylene glycol | 8 g | 8 g | 8 g |
| Ethylenediaminetetraacetic acid | — | — | 0.2 g |
| Pentasodium salt of ethylenetriaminepentaacetic acid | 2.4 g | 2.4 g | — |
| Ammonium thiolactate containing 50% of thiolactic acid | 1 g | 1 g | 0.8 g |
| 1-Phenyl-3-methylpyrazol-5-one | — | 0.2 g | 0.15 g |
| Homogentisic acid* | 0.4 g | 0.15 g | 0.3 g |
| 22° B strength ammonia solution | 5 cc | 7 cc | 10 cc |
| Water q.s.p. | 100 g | 100 g | 100 g |

*2,5-dihydroxyphenylacetic acid

Translucent liquid solutions are obtained, the appearance of which does not change during prolonged storage and which remain clear even when the bottles are opened.

At the time of use, 20 g of a 6% strength solution of hydrogen peroxide are incorporated into the same amount of these liquids; a very attractive gel then forms which can be applied to the hair; the coloration appears gradually and, after about thirty minutes, the head of hair is rinsed and then shampooed.

After rinsing and drying, the hair is uniformly dyed:

Composition A: On hair which is initially dyed light chestnut, a deep chestnut shade is obtained.

Composition B: A naturally deep blond head of hair containing a high percentage of white hair is dyed light chestnut.

Composition C: An entirely white head of hair is dyed golden coppery blond.

EXAMPLE 5

The following dyeing composition is prepared:

| | |
|---|---|
| Para-toluylenediamine base | 0.15 g |
| Para-aminophenol base | 0.1 g |
| 2-Methyl-5-[N-(β-hydroxyethyl)-amino]-phenol | 0.15 g |
| 1-Methoxy-3-nitro-4-[N-(β-hydroxyethyl)-amino]-benzene | 0.2 g |
| Pure cetyl alcohol | 18 g |
| Ammonium lauryl-sulphate containing 30% of active ingredient | 12 g |
| Cetyl/stearyl alcohol containing 15 mols of E.O. | 3 |
| Lauryl alcohol | 5 g |
| 22° B strength ammonia solution | 13 cc |
| Sodium salt of diethylenetriaminepentaacetic acid | 2 g |
| Homogentisic acid | 0.5 g |
| Water q.s.p. | 100 g |

EXAMPLE 6

| | |
|---|---|
| 4-[N-(β-Methoxyethyl)-amino]-aniline dihydrochloride | 0.4 g |
| Para-aminophenol base | 0.25 g |
| Resorcinol | 0.07 g |
| Meta-aminophenol | 0.04 g |
| 2-Methyl-5-[N-(β-hydroxyethyl)-amino]-phenol | 0.12 g |
| 2,4-Diaminophenoxyethanol dihydrochloride | 0.03 g |
| 1-Methoxy-3-nitro-4-[N-(β-hydroxyethyl)-amino]-benzene | 0.07 g |
| 1-(βHydroxyethyloxy)-3-nitro-4-aminobenzene | 0.06 g |
| Cetyl alcohol | 15 g |
| Partially sulphated cetyl/stearyl alcohol sold under the name "Lanette wax E" by Messrs. Henkel | 1 g |
| Polyoxyethyleneated castor oil | 1.8 g |
| Oleyl diethanolamide | 2.8 g |
| Perfume | 0.4 g |
| Ethylenediaminetetraacetic acid | 0.3 g |
| Homogentisic acid | 0.8 g |
| 22° B strength ammonia solution | 12 cc |
| Water q.s.p. | 100 g |

Creams are obtained which retain their consistency and their attractive appearance during storage and use.

At the time of use, 20 g of a milk containing 6% of hydrogen peroxide are incorporated into the same amount of cream and the mixture thus formed is applied to the hair; the coloration develops gradually and, after about thirty minutes, the head of hair is rinsed and shampooed.

After drying, the hair is uniformly dyed:

Composition 5: On naturally blond hair, a coppery light blond shade with a mahogany sheen is obtained.

Composition 6: Hair which is initially dyed deep blond is dyed golden light chestnut.

EXAMPLE 7

| CONSTITUENTS | 7A | 7B |
| --- | --- | --- |
| Para-toluylenediamine base | 1.7 g | 0.65 g |
| Para-aminophenol base | 0.3 g | 0.08 g |
| Resorcinol | 0.5 g | 0.25 g |
| Meta-aminophenol | 0.2 g | 0.08 g |
| 2,4-Diaminoanisole sulphate | 0.13 g | 0.02 g |
| Nitro-para-phenylenediamine | — | 0.03 g |
| Oxyethyleneated nonylphenol containing 4 mols of E.O., sold under the name "Remcopal 334" by Messrs. Gerland | 22 g | 22 g |
| Oxyethyleneated nonylphenol containing 9 mols of E.O., sold under the name "Remcopal 349" by Messrs. Gerland | 22 g | 22 g |
| Butylcellosolve | 8 g | 8 g |
| Propylene glycol | 8 g | 8 g |
| Diethylenetriaminepentaacetic acid (Na salt) | 2.4 g | 2.4 g |
| Ammonium thiolactate containing 50% of thiolactic acid | 0.8 g | — |
| 38° B strength sodium bisulphite solution | — | 1 cc |
| 1-Phenyl-3-methylpyrazol-5-one | 0.15 g | 0.15 g |
| 2-(2',5'-Dihydroxy-4'-methylphenyl)-acetic acid | 0.14 g | — |
| 3-(2',5'-Dihydroxy-4'-methylphenyl)-propionic acid | — | 0.145 g |
| 22° B strength ammonia solution | 5 cc | 5.5 cc |
| Water q.s.p. | 100 g | 100 g |

Translucent liquid solutions are obtained, the appearance of which does not change during prolonged storage and which remain clear even when the bottles are opened.

At the time of use, 20 g of a 6% strength solution of hydrogen peroxide are incorporated into the same amount of these liquids; a gel then forms which is applied to the hair. This gel retains its attractive appearance for a long time, whilst the colour develops gradually in the head of hair; after about thirty minutes, the head of hair is rinsed and then shampooed.

After rinsing and drying, the hair is uniformly dyed:
Composition 7A: On initially blond hair, a deep chestnut shade is finally obtained.

Composition 7B: An entirely white head of hair is dyed

EXAMPLE 8

| CONSTITUENTS | 8A | 8B |
| --- | --- | --- |
| Para-toluylenediamine base | 0.19 g | 0.19 g |
| Para-aminophenol | 0.16 g | 0.16 g |
| 4-(N-Methylamino)-phenol sulphate | 0.09 g | 0.09 g |
| Resorcinol | 0.07 g | 0.07 g |
| Meta-aminophenol | 0.04 g | 0.04 g |
| 2,4-Diaminoanisole sulphate | 0.03 g | 0.03 g |
| Nitro-para-phenylenediamine | 0.02 g | 0.02 g |
| Cetyl alcohol | 18 g | 18 g |
| Ammonium lauryl-sulphate containing 30% of active ingredient | 12 g | 12 g |
| Cetyl/stearyl alcohol containing 15 mols of ethylene oxide | 3 g | 3 g |
| Lauryl alcohol | 5 g | 5 g |
| Diethylenetriaminepentaacetic acid (Na salt) | 2.5 g | 2.5 g |
| 38° B strength sodium bisulphite solution | 0.7 cc | 0.7 cc |
| 2-(2',5'-Dihydroxy-4'-methylphenyl)-acetic acid | 0.46 g | — |
| 3-(2',5'-Dihydroxy-4'-methylphenyl)-propionic acid | — | 0.5 g |
| 22° B strength ammonia solution | 12 cc | 12 cc |
| Water q.s.p. | 100 g | 100 g |

Creams are thus obtained which retain their consistency and their attractive appearance during storage and use.

At the time of use, 30 g of a milk containing 6% of hydrogen peroxide are incorporated into 20 g of cream and the creamy mixture thus formed is applied to the hair.

The coloration develops gradually and, after about thirty minutes, the hair is rinsed and shampooed.

After drying, the hair is uniformly dyed: Composition 8A: On naturally deep blond hair, a restrained pearlescent golden light chestnut tint is obtained.

Composition 8B: Hair which is initially dyed light blond is dyed golden light chestnut.

EXAMPLE 9

| Paratoluylene diamine | 0.06 g |
| --- | --- |
| Paraaminophenol | 0.08 g |
| Resorcinol | 0.06 g |
| Metaaminophenol | 0.03 g |
| 1-Phenyl-3-methyl-5-pyrazolone | 0.15 g |
| Homogentisic acid | 0.12 g |
| Nonylphenol oxyethylenated with 4 moles of ethylene oxide sold under the name "Remcopal 334" by Messrs. Gerland | 27 g |
| Nonylphenol oxyethylenated with 9 moles of ethylene oxide sold under the name "Remcopal 349" by Messrs. Gerland | 22 g |
| 96° Ethyl alcohol | 16 g |
| Butylglycol | 5 cm³ |
| 22° B ammonia solution | 15 cm³ |
| Sodium bisulphite d = 1.32 | |
| Diethylenetriaminepentaacetic acid (Na salt) | 2.4 g |
| Water qsp | 100 |

The composition is applied to 90% white hair after dilution with the same quantity of 20 vol. hydrogen peroxide.

After leaving it for 30 minutes, the hair is shampooed and rinsed.

A very pale blond shade is obtained.

EXAMPLE 10

| Paraphenylene diamine | 0.07 g |
| --- | --- |
| Paraaminophenol | 0.02 g |
| 2,6-Dimethyl-5-acetylaminophenyl | 0.06 g |
| Resorcinol | 0.8 g |
| 6-Hydroxybenzomorpholine | 0.02 g |
| 2-Methyl-5-methoxyparaphenylene diamine | 0.02 g |
| 2-Methyl-5-(N-β-hydroxyethyl)aminophenol | 0.02 g |
| 1-Phenyl-3-methyl-5-pyrazolone | 0.15 g |
| 3-[(2',5'-Dihydroxy)phenyl]propionic acid | 0.2 g |
| Nonylphenyl oxyethylenated with 4 moles of ethylene oxide sold under the name "Remcopal 334" by Messrs. Gerland | 27 g |
| Nonylphenol oxyethylenated with 9 moles of ethylene oxide sold under the name "Remcopal 349" by Messrs. Gerland | 22 g |
| 96° Ethyl alcohol | 16 g |
| Butylglycol | 5 g |
| 22° B ammonia solution | 12 cm³ |
| Sodium bisulphite d = 1.32 | 1 cm³ |
| Diethylenetriaminepentaacetic acid (Na salt) | 2.4 g |
| Water qsp | 100 g |

This composition is applied to 90% white hair, after dilution with the same quantity of 20 vol. hydrogen peroxide. After leaving it for 30 minutes, the hair is shampooed and rinsed. A very pale burnt blonde shade is obtained.

EXAMPLE 11

| | |
|---|---|
| Paratoluylene diamine | 2.3 g |
| Metadiaminoanisole sulphate | 2 g |
| Resorcinol | 0.2 g |
| Metaaminophenol | 0.6 g |
| 2-Ureido-4-hydroxy-4'-amino-diphenylamine | 0.9 g |
| Stearyl alcohol | 20 g |
| Coconut monoethanolamide | 5 g |
| Ammonium laurylsulphate containing 20% fatty alcohol | 10 g |
| 22° B ammonia solution | 10 cm$^3$ |
| Diethylene-triamine pentaacetic acid (sodium salt) | 2.4 g |
| Thioglycolic acid | 0.5 cm$^3$ |
| 2-[(2',5'-Dihydroxy-3',4'-dimethyl)phenyl]acetic acid | 2 g |
| Water qsp | 100 g |

This composition is applied to 90% white hair after dilution with 1½ times the quantity of 20 vol. hydrogen peroxide.

After leaving for 30 minutes the hair is shampooed and rinsed.

A blue-black shade is obtained.

The pH of the compositions described in Examples 4 to 11 is about 9.5 after mixing with the oxidant.

We claim:

1. A composition suitable for dyeing human hair, consisting essentially of at least one oxidative dyestuff and, as anti-oxidant, a 2,5-dihydroxyphenylalkanoic acid or a salt thereof corresponding to the general formula:

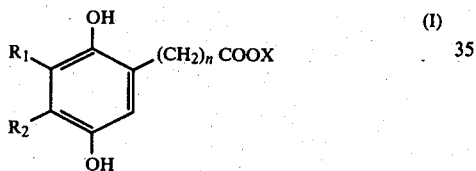

in which $R_1$ and $R_2$ are identical or different and denote hydrogen or a straight- or branched-chain alkyl group of 1 to 4 carbon atoms, X denotes hydrogen, an alkali metal, ammonium, or an alkanolamine radical and n is an integer from 1 to 4.

2. A composition according to claim 1 in which $R_1$ or $R_2$ denotes a methyl, ethyl or propyl group, and X denotes sodium, potassium or a monoethanolamine, diethanolamine or triethanolamine radical.

3. A composition according to claim 1 in which at least one of $R_1$ and $R_2$ denotes a said alkyl group.

4. A composition according to claim 1 in which the 2,5-dihydroxyphenylalkanoic acid is selected from the group consisting of 2-(2',5'-dihydroxy-4'-methyl-phenyl)-acetic acid, 2-(2',5'-dihydroxy-3',4'-dimethylphenyl)-acetic acid and 3-(2',5'-dihydroxy-4'-methylphenyl)-propionic acid.

5. A composition according to claim 1 in which the 2,5-dihydroxyphenylalkanoic acid is selected from the group consisting of homogentisic acid and 2-(2',5'-dihydroxy phenyl)propionic acid.

6. A composition according to claim 1 which contains 0.05 to 5% weight of a 2,5-dihydroxyphenylalkanoic acid or salt thereof of formula (I).

7. A composition according to claim 6 which contains 0.1 to 3% by weight of a 2,5-dihydroxyphenylalkanoic acid or salt thereof of formula (I).

8. A composition according to claim 1 which additionally includes a sulphite, mercaptan or pyrazolone antioxidant.

9. A composition according to claim 8 in which the antioxidant is selected from the group consisting of sodium bisulphite, thioglycolic acid and thiolactic acid or a salt thereof, and 1-phenyl-3-methylpyrazol-5-one.

10. A composition according to claim 8 in which the sulphite or mercaptan is present at a concentration not exceeding 1% by weight.

11. A composition according to claim 1 which additionally includes a nitro benzene series, azo or anthraquinone direct dyestuff at a concentration from 0.005% to 3% by weight.

12. A composition according to claim 11 in which the direct dyestuff is selected from nitrophenylenediamines, nitroaminophenols, dinitroaminophenols, dinitroaminobenzenes, nitroaminobenzenes and nitrodiphenylamines.

13. A composition according to claim 1 in which the at least one oxidative dyestuff is an oxidative base selected from the group consisting of para-phenylenediamines, para-aminophenols, ortho-phenylenediamines, orthoaminophenols, substituted and unsubstituted heterocyclic bases and bases corresponding to the general formula:

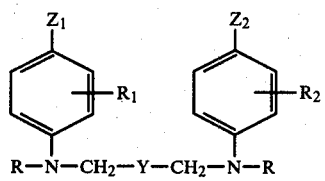

in which: $Z_1$ and $Z_2$ are identical or different and represent a hydroxyl group or —$NHR_3$ group in which $R_3$ denotes a hydrogen atom or a lower alkyl radical; $R_1$ and $R_2$ are identical or different and represent a hydrogen or halogen atom or an alkyl group; R represents a hydrogen atom, an alkyl or hydroxyalkyl group or an aminoalkyl group or an aminoalkyl group in which the amino radical is substituted; and Y represents a radical of the formula:

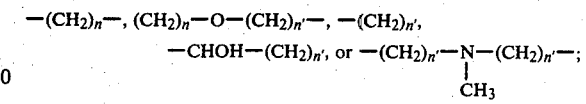

n being 0 or an integer from 1 to 8 and n' being 0 or an integer from 1 to 4, or an acid addition salt of a said base.

14. A composition according to claim 13 in which the oxidative base is present at a concentration from 0.005% to 10% by weight.

15. A composition according to claim 14 in which the oxidative base is present at a concentration from 0.01% to 5% by weight.

16. A composition according to claim 1 which additionally includes one or more phenol, metadiphenol, meta-aminophenol or meta-diamine coupler, or salt thereof.

17. A composition according to claim 1 which additionally includes one or more of α-naphthol, 6-hydroxybenzomorpholine, 6-aminobenzomorpholine, 2,6- diaminopyridine, a pyrazolone or diketone coupler, or a salt thereof.

18. A composition according to claim 16 or 17 in which the coupler is present at a concentration from 0.005 to 5% by weight.

19. A composition according to claim 16 or 17 in which the coupler is present at a concentration from 0.01 to 3% by weight.

20. A composition according to any one of claims 1 to 19, which additionally includes a leuco derivative of an indoaniline at a concentration from 0.005 to 4% by weight.

21. A composition according to claim 1 in the form of a gellable composition, which additionally includes, in an aqueous vehicle, a polyoxyethyleneated or polyglycerolated non-ionic compound at a concentration of 5 to 60% by weight, or a soap of a liquid fatty acid at a concentration from 0.5 to 15% by weight, and a solvent at a concentration of 2 to 20% by weight and an alkalising agent.

22. A composition according to claim 1 in the form of a cream which additionally includes, in an aqueous vehicle, a soap of a natural or synthetic $C_{12}$ to $C_{18}$ fatty acid at a concentration of 10 to 30% by weight, or a natural or synthetic $C_{12}$ to $C_{18}$ fatty alcohols at a concentration of 5 to 25% by weight, an emulsifier at a concentration of 1 to 25% by weight, and an alkalising agent.

23. A composition according to claim 21 or 22 which contains a sequestering agent, thickener or perfume.

24. A composition according to claim 1 which has a pH of 6 to 11.

25. A composition according to claim 24 which has a pH of 8 to 11.

26. A composition according to claim 22 which additionally includes a fatty amide at a concentration of up to 10% by weight.

27. A composition according to claim 26 which contains a sequestering agent, thickener or perfume.

28. Process for dyeing human hair which comprises mixing at the time of use a composition as defined in claim 1 with a cosmetic oxidising agent and applying the mixture to the hair, leaving it thereon for 5 to 45 minutes, and then rinsing and drying the hair.

* * * * *